United States Patent
Bergh et al.

(10) Patent No.: US 11,033,739 B2
(45) Date of Patent: Jun. 15, 2021

(54) MOTION TRAINING AID WITH STIMULATOR

(71) Applicant: West & Bergh Holding AB, Malamö (SE)

(72) Inventors: Christian Bergh, Höllviken (SE); Christian Wallenberg, Malmö (SE); Philip Dahl, Lund (SE)

(73) Assignee: West & Bergh Holding AB

( * ) Notice: Subject to any disclaimer, the term of this patent is extended or adjusted under 35 U.S.C. 154(b) by 0 days.

(21) Appl. No.: 17/136,880

(22) Filed: Dec. 29, 2020

(65) Prior Publication Data

US 2021/0113839 A1  Apr. 22, 2021

Related U.S. Application Data

(63) Continuation of application No. 16/790,419, filed on Feb. 13, 2020, now Pat. No. 10,905,880, which is a (Continued)

(51) Int. Cl.
*A61N 1/36* (2006.01)
*A63B 71/06* (2006.01)
*A63B 24/00* (2006.01)

(52) U.S. Cl.
CPC ..... *A61N 1/36034* (2017.08); *A61N 1/36031* (2017.08); *A63B 71/0622* (2013.01); (Continued)

(58) Field of Classification Search
CPC ............ A61N 1/36034; A61N 1/36031; A63B 71/0622; A63B 2024/0009; (Continued)

(56) References Cited

U.S. PATENT DOCUMENTS

2004/0064157 A1  4/2004 Norton
2011/0270337 A1  11/2011 Doerr et al.
(Continued)

FOREIGN PATENT DOCUMENTS

CN  101631589 A  1/2010
CN  103212188 A  7/2013
(Continued)

OTHER PUBLICATIONS

Chinese Office Action for Application No. 201780097057.X dated Jan. 22, 2021.

*Primary Examiner* — Robert P Bullington
(74) *Attorney, Agent, or Firm* — Tarolli, Sundheim, Covell & Tummino LLP

(57) ABSTRACT

A training aid stimulator for providing fast perceptive feedback is disclosed. The training aid stimulator includes a first skin electrode and a second skin electrode both for making electrical contact to the body of a user, a charging module, a discharge module connected to one or more of the skin electrodes for a feedback discharging, and a processor for controlling the charging of a capacitor equivalent to a predetermined first voltage level, wherein the processor further being connected to the discharge module for controlling a feedback discharge of the capacitor equivalent. The stimulator comprises a voltage measurement module for measuring the level of charge of the capacitor equivalent, and the processor is configured for keeping the stimulator ready to discharge by repeatedly measuring the level of charge and by providing a maintenance charging when the voltage over said capacitance equivalent is at or below a predetermined second voltage level.

11 Claims, 7 Drawing Sheets

Related U.S. Application Data continuation of application No. PCT/EP2017/080677, filed on Nov. 28, 2017.

(52) U.S. Cl.
CPC .............. *A63B 2024/0009* (2013.01); *A63B 2024/0015* (2013.01); *A63B 2071/0655* (2013.01); *A63B 2220/803* (2013.01)

(58) Field of Classification Search
CPC .... A63B 2024/0015; A63B 2071/0655; A63B 2220/803
USPC .......................................................... 607/48
See application file for complete search history.

(56) References Cited

U.S. PATENT DOCUMENTS

| | | | |
|---|---|---|---|
| 2014/0199672 A1 | 7/2014 | Davidson | |
| 2015/0081057 A1 | 3/2015 | Hamada et al. | |
| 2015/0105841 A1 | 4/2015 | Chambers et al. | |
| 2018/0140859 A1* | 5/2018 | Meir | A61N 1/3968 |

FOREIGN PATENT DOCUMENTS

| | | |
|---|---|---|
| CN | 205434693 U | 8/2016 |
| CN | 106730604 A | 5/2017 |
| WO | 2014030849 A1 | 2/2014 |
| WO | 2014138990 A1 | 9/2014 |

* cited by examiner

MOTION TRAINING AID WITH STIMULATOR

RELATED APPLICATIONS

This application is a continuation of pending U.S. patent application Ser. No. 16/790,419 filed on Feb. 13, 2020, which is a non-provisional application under 35 USC 111(a), claiming priority to International Serial No. PCT/EP2017/080677, filed on Nov. 28, 2017, the entirety of which both are herein incorporated by reference.

TECHNICAL FIELD

The present invention relates to the field of training aids, i.e., devices that helps a person or animal better perform some activity of that person or animal. More particularly the present invention relates to motion training aids, i.e., systems or devices that provide some kind of feedback relating to a motion performed by the user. Even more particularly it relates to sports movements training aids.

PRIOR ART

One example of motion training aid is known from WO2003024544. It discloses a repetitive motion feedback system provided with various sensors and devices for monitoring aspects of a repetitive motion sequence, such as a golf swing. The monitored aspects can include motion properties of an object moved by the user, position properties of the user and motion properties of the user. A data processing system for receiving data of the monitored aspects provides feedback data that is provided to a feedback output device, such as a graphical display device or speaker, so that the user is provided with feedback regarding the repetitive motion sequence. In one particular embodiment, the user's performance is compared to a template of a prior performance, with feedback being provided regarding the differences.

Another prior art document is U.S. Pat. No. 6,778,866 disclosing a method and apparatus for teaching a person how to perform a specific body motion in a consistent manner is based on electronically measuring one or more parameters of an actual body motion, comparing the one or more measured parameters with corresponding parameters of a target body motion, and providing a sensible feedback to the user based on a degree of correspondence between the one or more measured parameters and the corresponding target parameters. In a particular embodiment, the feedback is audible. More specifically the feedback is a musical tune that has a particular characteristic (such as rhythm) that is particularly suited to a particular body motion (such as a golf swing). The feedback may be in the form of electronically causing the musical tune to go off-key in proportion to a discrepancy between the actual body motion and the target body motion.

A further prior art system and method for teaching ergonomic motion of an athlete, for example a golfer is disclosed in WO200518759. The system including the video camera for capturing successive image of the golfer executing a preferring golf swing and a threshold definition system that allows the golfer define a spatial region of the video image. If the spatial region is intruded upon, an alarm is actuated, thereby providing feedback so the golfer may alter the technique of the next attempted motion. For example, the golfer may define the region such that if the club moves off plane during a swing, a tee removal system causes the ball to disappear. In this manner, the golfer is only able to hit the ball when the club stays on plane.

SUMMARY OF THE INVENTION

The inventors are aiming at providing a device for providing fast feedback for training devices used to train and perfect some kind of user behaviour, or action, wherein this behaviour or action is happening relatively quickly. Examples of such behaviours or actions include but are not limited to e.g. sports motions, such as technically complex motions occurring in e.g. athletic field events (high jump, pole vault, hammer throw, javelin throw etc), or gymnastics (jumps, choreography, cheerleading moves), or baseball, or golf (golf swing, putting stroke), just to mention a few.

The inventors have devised that it is desirable that a feedback signal signalling a less efficient move, or a "bad" move, or a movement that deviates from a reference movement should be instantaneous, or at least perceived as instantaneous by the user. The stimulus unit of an embodiment of the present invention is configured to deliver the stimulus with very short delay, preferably, less than 50 ms, or more preferred less than 20 ms, or most preferred less than 10 ms. The stimulus should also be distinct. The inventors are aiming at providing a noticeable and distinct feedback in order to indicate and point out an undesirable motion to discourage said undesirable motion by the user.

In various embodiments, the stimulus unit comprises a charging module and a discharge module and body electrodes. The charging module is configured to charge a capacitor equivalent that may comprise a "body capacitance" inherent to the body of a person, or a charge holding capacitor. The charging module is configured to charge the capacitor equivalent to a charging level that is sufficient to cause, at discharge, a sensory sensation, i.e., an electric shock sensation or similar sensation to the person or animal performing the activity. The discharge is supposed to be triggered when there is detected a disagreement between the position values of a current motion and of a predetermined desired motion. The level of charge or the voltage of the capacitor equivalent is measured and further charge is supplied when necessary to maintain a level that is sufficient to provide the electric shock or similar sensation.

Thus, in alternate embodiments different couplings may be provided to utilize separate capacitor couplings or utilizing the inherent body capacitance of a user. There is also disclosed electrical couplings to provide an efficient stimulus signal to the user, as well as the signal itself.

The stimulator unit may further be provided with a particular circuit to connect and disconnect a measurement module so as to save energy by not letting electrical charge leak out through the measurement module.

BRIEF DESCRIPTION OF THE DRAWINGS

In order that the manner in which the above recited and other advantages and objects of the invention are obtained will be readily understood, a more particular description of the invention briefly described above will be rendered by reference to specific embodiments thereof which are illustrated in the appended drawings.

Understanding that these drawings depict only typical embodiments of the invention and are not therefore to be considered to be limiting of its scope, the invention will be described and explained with additional specificity and detail through the use of the accompanying drawings in which:

FIG. 3a shows a more detailed principal circuit diagram of the stimulator device of FIG. 2a.

DETAILED DESCRIPTION

Definitions

Figure 1A:
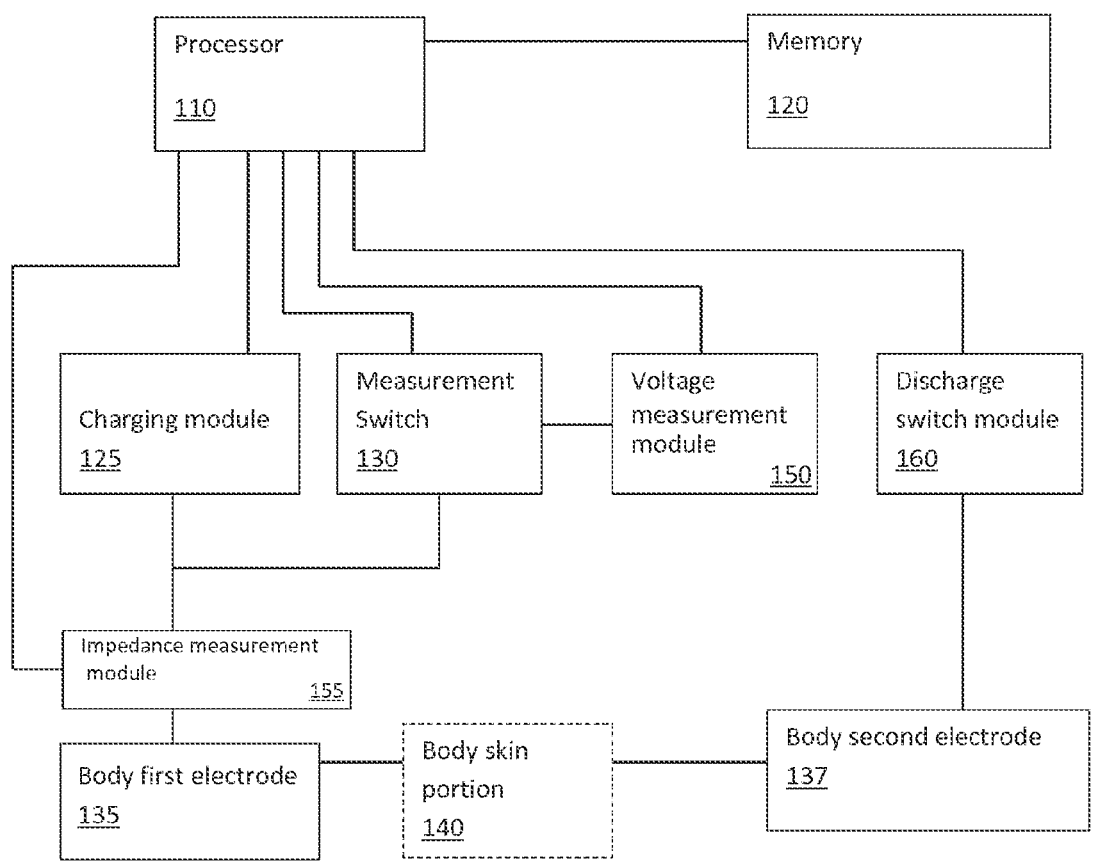
FIG. 1a shows a block diagram of a stimulator device according to an embodiment of the present invention.

For the purpose of the present invention, and in the following text, the following terms are used with the meaning as explained below.

"Motion representation": A "motion representation" is a usually mathematical representation of a motion. The motion representation may include representations of linear and rotational motion position, motion velocity, and motion acceleration. For example, the motion may be represented by the current position of a predetermined point on the body of a user, or the motion may be represented by a (motion) track, see below.

"Position": With the term "position", as used herein is understood the physical local position of a sensor unit or small object in relation to a nearby reference point, and expressed using a suitable coordinate system. Typically, in the context of the present invention, positions are within the magnitude of 0-5 meters from the reference point.

"Undesired motion": The term "undesired motion" is used to denote a motion that is undesired or comprises an undesired feature as seen from the point of view of the user, and/or his or her coach.

"Body motion tracker": As used herein, the term "body motion tracker" denotes a device or a system, or a piece of computer code when executed capable of tracking one or more predefined points of a user's body over time, based on processed sensor data.

"Tracking": With the term "tracking" is understood the activity of collecting and storing (recording) consecutive positions of one or more predefined points on a user's body during a motion.

"Motion track": With the term "motion track" is meant the result of the tracking activity, i.e., the collective amount of stored consecutive positions of a predefined body point over time, starting at a start point or start time, and ending at a finishing point or finishing time.

"Reference motion track": A "reference motion track" is a desired motion track that can be used to create a model to which motion representations of motions can be compared.

"Rotation angle" or "Angle of rotation": In two dimensional space the "angle of rotation" is a measurement of the amount, the angle, by which an object is rotated about a fixed point. In three-dimensional space rotation is measured and indicated using angles of rotation about three coordinate axes.

"Predefined body point": With the term "predefined body point" is meant a point on a user's body that has been provided with means for facilitating the tracking of said point, e.g. a sensor unit.

"Attitude": In the context of the present invention the term "attitude" is used to denote an object's orientation (attitude, angular position) in space. The attitude may be represented by pitch, yaw and roll angles or, alternatively, by an attitude vector or axis, and a rotation angle around that vector or axis, i.e. axis-angle representation, c.f. Euler's rotation theorem.

"Motion sensor unit": A "motion sensor unit" is understood to be a unit, attachable to a user's body, that are able to deliver motion information, such as accelerations, information making it possible to determine the sensor's attitude and three-dimensional position or changes in the same position during a motion of the user, in a suitable reference system. The sensor unit is conceived to be small and lightweight enough not to interfere with the motion of the user.

"Control unit": In the context of the present invention a "control unit" is a unit comprising a man-machine interface for operating a device, it also usually comprises wireless communication means to communicate with the processor and/or the motion sensor unit.

"Sample": In the context of the present invention the term "sample" is used to denote a calculated state of the motion sensor unit at a particular moment in time, and may include representations of linear and/or rotational: motion position, motion velocity, and motion acceleration as calculated by the processor based on motion sensor data from the motion sensor unit and also based on a reference frame, i.e., a coordinate system. Associated with the sample is a sample number and/or a sample time.

"Processor": In the context of the present invention the term "processor" is used to denote a processor system irrespective if it comprises one or more logical or physical processors, if nothing else is explicitly mentioned.

"Memory": In the context of the present invention the term "memory" is used to denote a memory system irrespective if it comprises one or more logical or physical memories, if nothing else is explicitly mentioned "Stimulator": In the context of the present invention the term stimulator is used to denote a device, attachable to the body of a person or animal, and upon receiving a command, capable of eliciting a stimulus perceptible by that person or animal.

"Motion": With the term "motion" is understood any body movement performed by a person, composite or simple, may it be a movement of one or more of his or her extremities, or torso, or centre of gravity. Any possible ambiguities should be solved by the context in which the term is used. The term is also used to denote the movement as sensed by a sensor. Example motions include portions of or complete high jump, pole vault, hammer throw, javelin throw, gymnastics jumps, choreography moves, cheerleading moves, baseball batting, baseball pitching, golf swing, putting stroke.

The stimulus unit is configured to deliver the stimulus with very short delay, preferably, less than 50 ms, or more preferred less than 20 ms, or most preferred less than 10 ms. The stimulus should also be distinct.

In order to be able to deliver the stimulus, i.e., an electric discharge, with short notice, there is provided a training aid stimulator device as outlined in FIG. 1a, The block diagram in FIG. 15 shows a stimulator device according to an embodiment of the present invention. A processor 110 is connected to a memory 120. Further, the processor is connected to a charging module 125 for instructing the charging module 125 to charge. The charging module 125 is connected to a first body electrode 135 to provide charge to charging a body capacitance connected via the first body electrode 135. The charging module 125 may be connected to the first body electrode via an impedance measurement module 155, this will be discussed later.

Further the processor 110 is connected to a measurement switch 130. The measurement switch is controlled by the processor to connect and disconnect a voltage measurement module 150 to the first body electrode 135 at certain times. The timing of the connecting and disconnecting respectively of the measurement module to the first body electrode 135 will be further explained below. The processor 110 is further connected to a discharge module 160 in order to control the delivery of a discharge of the body capacitance connected via the first body electrode 135 and a second body electrode 137. The discharge switch module 160 is configured to connect the body second electrode 137 to ground upon commanded so from the processor 110, to effectively cause a discharge through the skin of a subject using the stimulator.

Figure 1B:
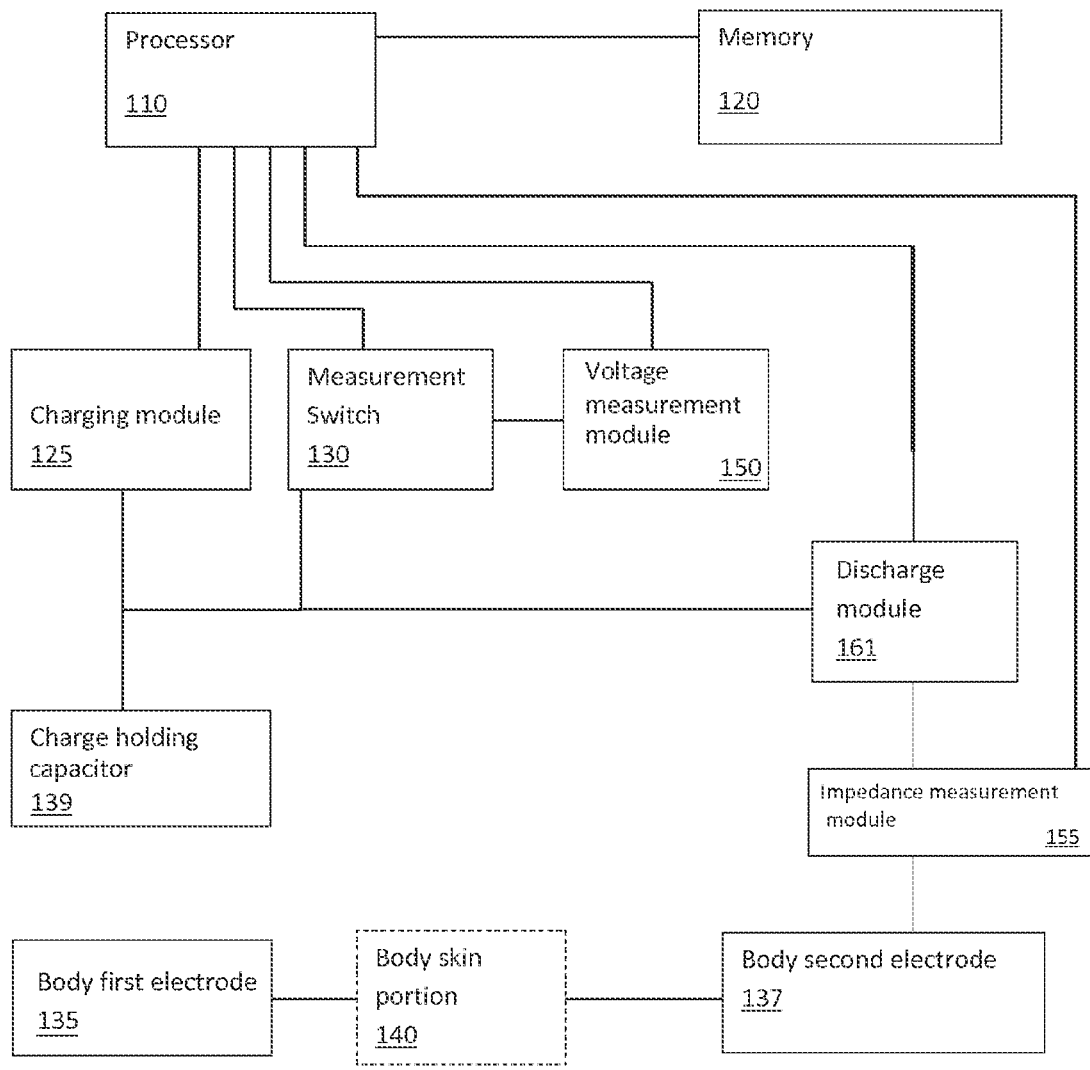
FIG. 1b shows a block diagram of a stimulator device according to a further embodiment of the present invention.

The block diagram in FIG. 1b shows a stimulator device according to second embodiment of the present invention, A processor 110 is connected to a memory 120. Further, the processor is connected to a capacitor charging module 125 for charging a charge holding capacitor 139, C1. A first electrode of the charge holding capacitor is connected to the capacitor charging module 125. A second electrode of the charge holding capacitor 139, C1 is connected to ground. Further, the processor 110 is connected to a measurement switch 130. The measurement switch is controlled by the processor to connect and disconnect a voltage measurement module 150 to the first electrode of the charge holding capacitor 139, C1 at certain times. C1 is dimensioned to be able to hold a charge sufficient to be able to cause a clearly perceivable feedback sensation with the user, when C1 is discharged.

The timing of the connecting and disconnecting respectively of the voltage measurement module 150 to the first electrode of the charge holding capacitor 139 will be further explained below.

The processor 110 is further connected to a discharge module 161 in order to control the delivery of a discharge of the charge holding capacitor 139 connected via a second body electrode 137, the skin 140 of a user and a first body electrode 135. The discharge module 161 is arranged to connect the body second electrode to the first electrode of the charge holding capacitor 139, possibly via an impedance measurement module 155, upon commanded so from the processor 110. The first body electrode 135 in this embodiment preferably connected to ground.

An advantage of this coupling is that charge deposited in the charge holding capacitor 139 can be kept isolated from the body until discharge, and thus isolated from a risk of possible electrical leakage associated with biological tissue.

Figure 1C:
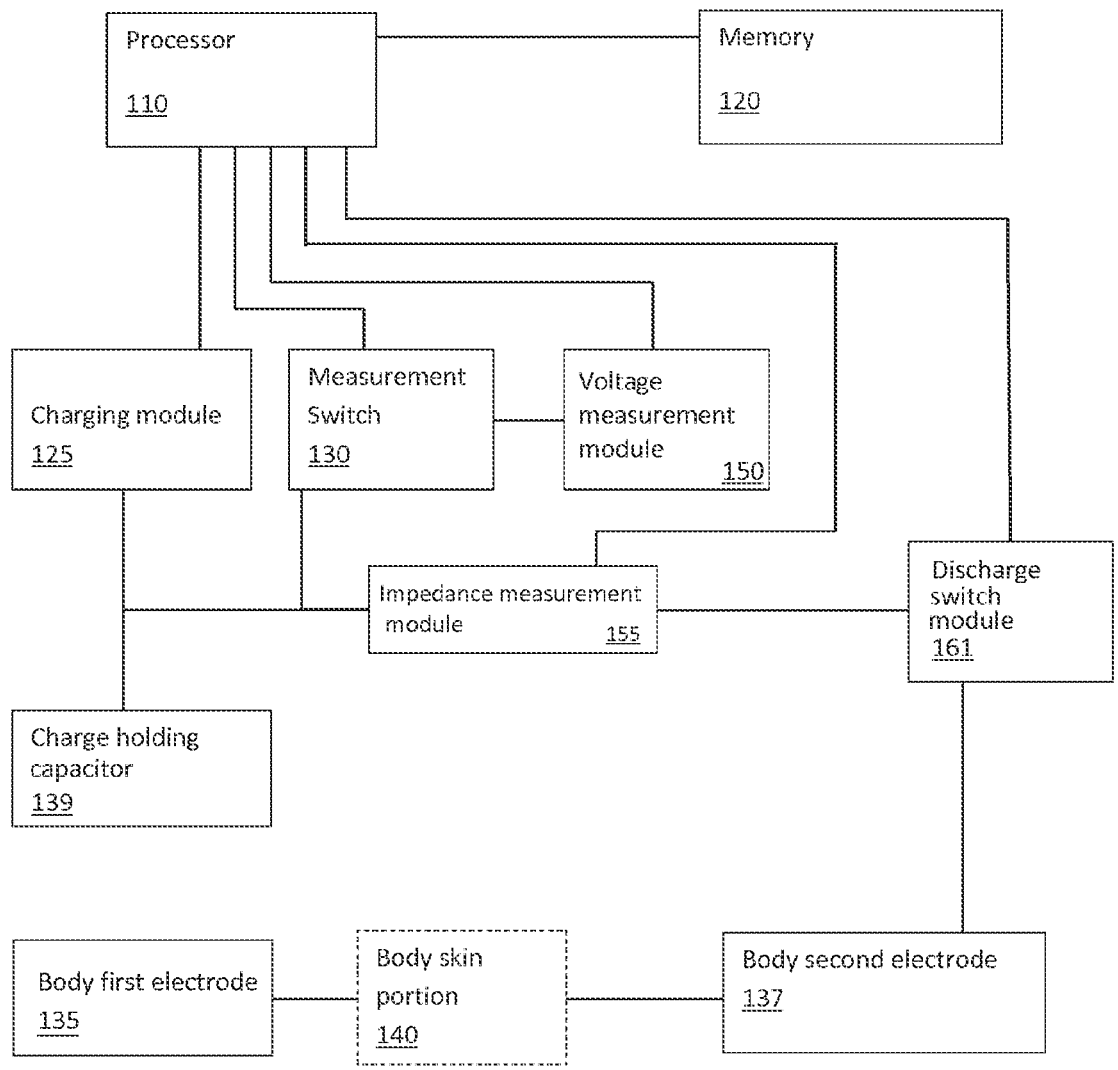
FIG. 1c shows a block diagram of a stimulator device according to a still further embodiment of the present invention.

FIG. 1c will be described later in context of impedance measurements.

Figure 2A:
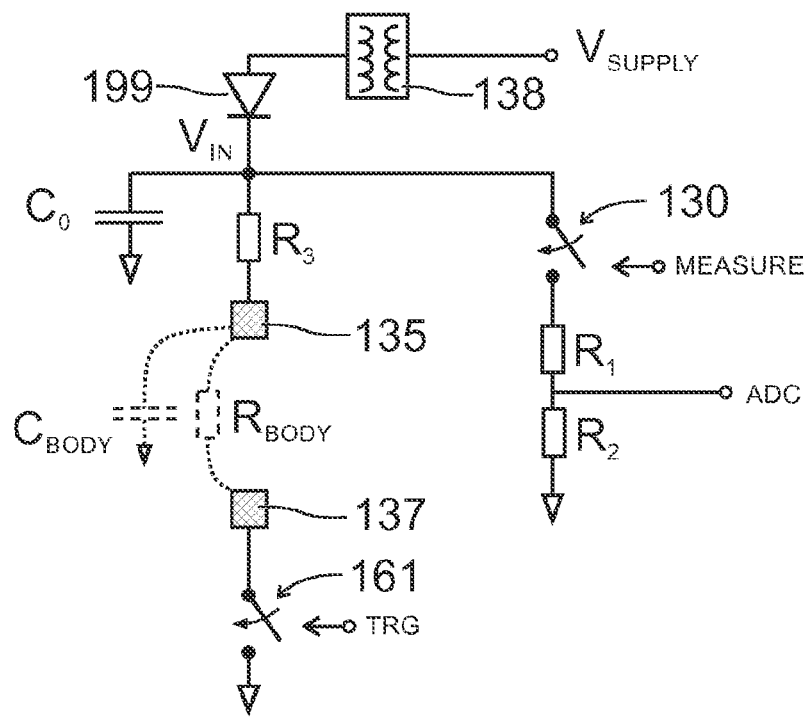
FIG. 2a shows a principal circuit diagram of a first basic embodiment of a stimulator device.
Figure 3A:
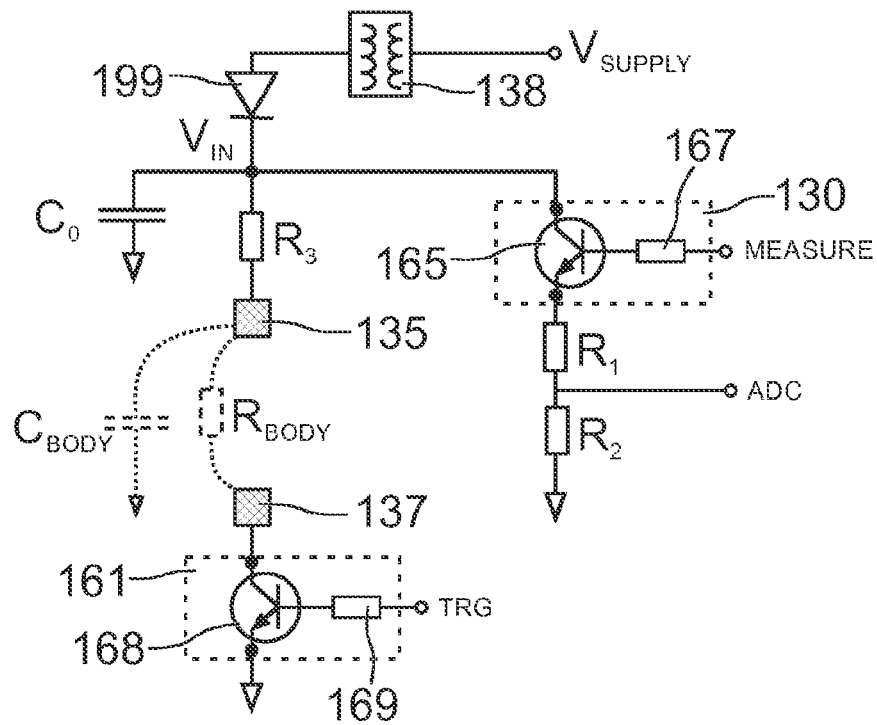

FIGS. 2a, and 3a show alternate principal wiring diagrams for a first circuit, and a second circuit capable of providing a distinct biofeedback electrical stimulus to the skin of a user. FIG. 2a shows a stimulator circuit comprising a first electrode 135 and a second electrode 137 devised to make contact to the skin of a user. Said first and said second electrodes can also be referred to as skin electrodes. Power at a low voltage level is supplied at $V_{SUPPLY}$. The low voltage normally is DC (Direct Current) supplied by a battery which is stepped up in a transformer device 138 to a higher level, $V_{IN}$. In various embodiments, the transformer device 138 comprises a DC-to-DC converter or an electric power converter. A diode 199 is provided after the transformer device 138 and connected to connection point $V_{IN}$. A measuring switch 130 is connected between $V_{IN}$ and a first resistor $R_1$ of a voltage divider. The voltage divider is made up of the first resistor $R_1$ and a second resistor $R_2$. An analogue to digital converter ADC is connected between the resistors $R_1$ and $R_2$ and could be said to constitute a voltage measurement module 150 together with these resistors. The measuring switch 130 is connected to and controlled by a signal MEASURE from the processor 110. An electrical model for the stimulator circuit as attached to the human skin has been devised. The model includes a capacitance of the body, $C_{BODY}$, and a resistance $R_{BODY}$ of the skin between said first electrode 135 and said second electrode 137.

The stimulator circuit further comprises a discharge switch 161 for controlling a feedback discharge also called a biofeedback electrical stimulus. The discharge switch 161 is connected between the second skin electrode 137 and earth to provide a discharge drain when triggered by a trigger signal from trigger output, TRG, of the processor. When a voltage is applied at $V_{SUPPLY}$ and increased in the transformer device 138 the capacitance of the body, $C_{BODY}$, will be charged to a predetermined level. The actual level is measured by applying the signal MEASURE and reading a voltage signal in the voltage divider at ADC. An analogue to digital converter can be used to provide the processor 110 with the actual reading of voltage level. When the predetermined level is reached the processor 110 is ready to provide a signal at TRG to open the discharge switch 161. As a result, the capacitance $C_{BODY}$ is discharged and a pulse is experienced by the person carrying said first electrode 135 and said second electrode 137.

Figure 4:
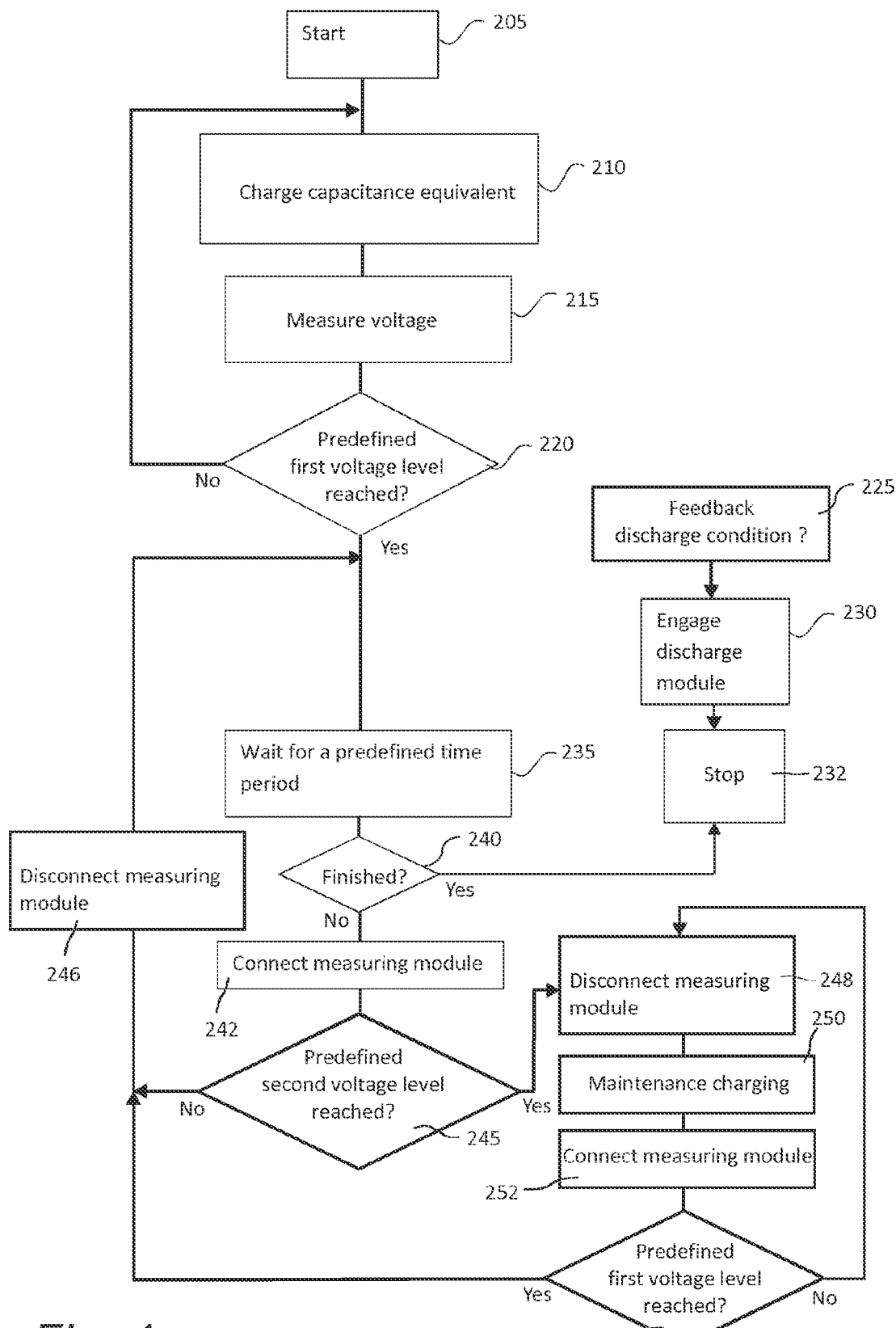
FIG. 4 shows a flowchart over method steps for providing stimulation feedback.

The TRG signal is delayed until a specific condition is present. A continuous discharge through first resistor $R_1$ and second resistor $R_2$ is avoided in the embodiment shown in FIG. 2a by opening the measuring switch 130. In the embodiment shown in FIG. 3a an implementation of the measuring switch 130 comprises a first transistor 165 connected at a control input to a first control resistor 167 receiving the MEASURE signal. In a similar way, the discharge switch 161 comprises a second transistor 168 connected at a control input to a second control resistor 169 provided for receiving the TRG signal from the processor. Still, there will be some minor continuous discharging from $C_{BODY}$, but by a maintenance or support charging as described below with reference to FIG. 4 and FIG. 5 this problem can be avoided.

The process of maintenance charging (support charging or top-up charging) is started in block 205 and the charging is started in block 210. The processor 110 then applies signal MEASURE to the measuring switch and the voltage over second resistor $R_2$ is measured in block 215. In block 220 it is checked whether a predefined first voltage level is reached. If the predefined first voltage level is not reached the charging in block 210 continues. If the predefined first voltage level is reached the processor continuously awaits a condition for a feedback discharge in block 225, When a condition for discharge is at hand the discharge module 160 is activated in block 230. The device then is stopped in block 232. If there is no condition for discharge the processor enters a wait condition for a predetermined time period in block 235.

Figure 5:
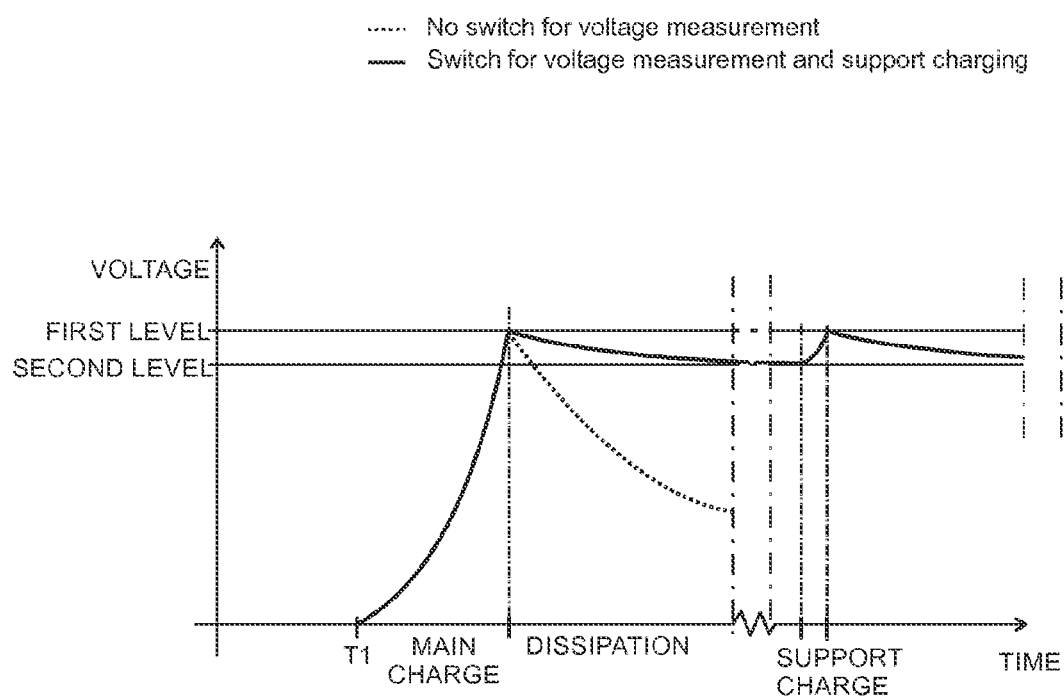
FIG. 5 is a diagram showing voltage as a function of time during a charging process used in a stimulator device according to an embodiment of the present invention.

The processor then checks if the full process is finished in block 240. If the process is finished, the charge of the body capacitance is slowly dissipated, and the device then is stopped in block 232. If the process is still in operation (motion continues) the voltage measurement module 150 is activated in block 242 and it is checked in block 245 whether voltage of voltage divider $R_1$, $R_2$ has dropped to or below a predetermined second level, c.f. FIG. 5. If voltage has not dropped to or below said predetermined second level the measuring module is switched off in block 246 and the process returns to block 235.

If voltage has dropped to or below said predetermined second level the measuring module is switched off in block 248 to preserve charge. Then maintenance charging is activated in block 250. The maintenance charging is maintained for a predetermined time period after which the voltage measurement module 150 is activated in block 252, In block 254 it is checked whether the predefined first voltage level is reached. If the predefined first voltage level is not reached the measuring module is disconnected in block 248 and the maintenance charging in block 250 continues. If the predefined first voltage level is reached the measuring module is disconnected in block 246 and the process returns to block 235.

Figure 2B:
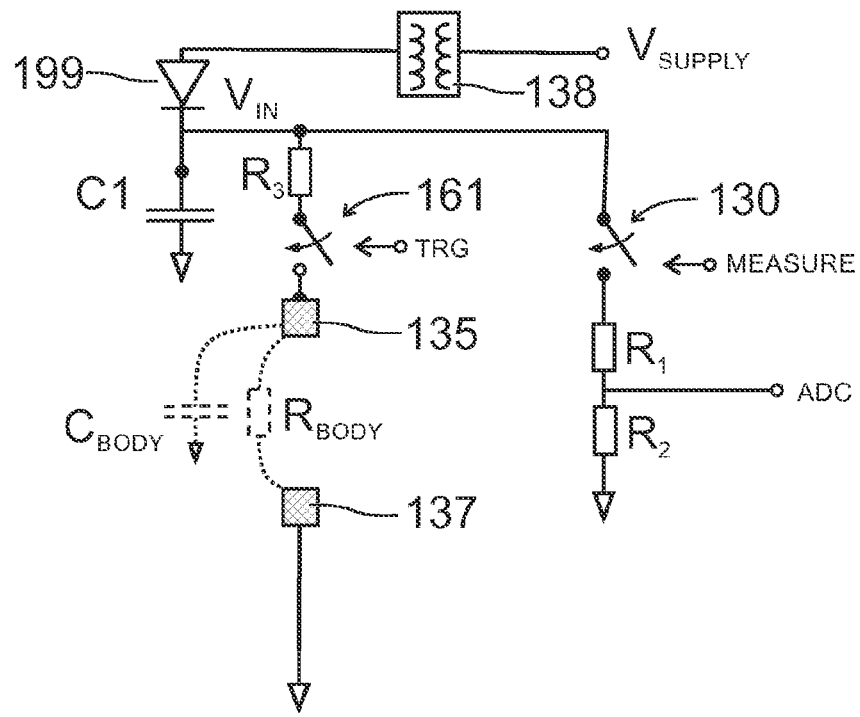
FIG. 2b shows a principal circuit diagram of a second basic embodiment of a stimulator device.
Figure 3B:
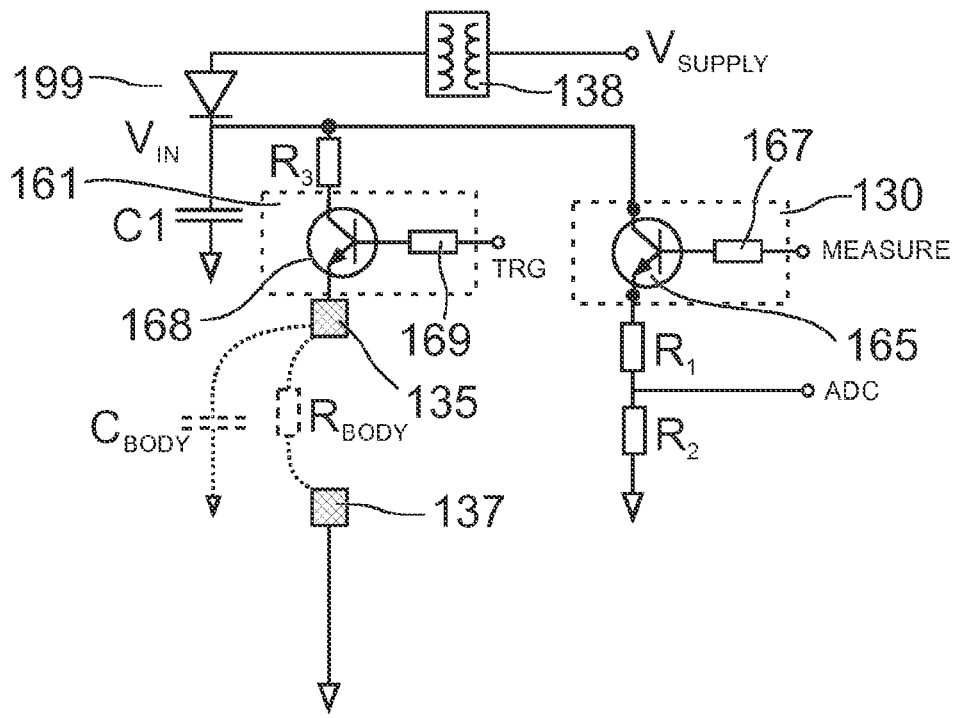
FIG. 3b shows a more detailed principal circuit diagram of the stimulator device of FIG. 2b.

FIGS. 2b and 3b shows corresponding principal wiring diagrams for embodiments wherein a discharge switch module 161 is arranged electrically close to the first electrode 135, thereby effectively isolating the body from the charging voltage and a charge holding capacitor 139, C1.

The diagram of FIG. 5 shows a diagram of voltage vs time during the charging and maintenance charging processes described above with reference to FIG. 4. A main charge process corresponding to the charge block 210 is initiated at time T1. When the predetermined first voltage level is reached, a discharge process starts. The dotted line indicates the discharge that would take place, should the measurement switch 130 be omitted. The voltage level in that case soon would reach a level where a controlled discharge would not be sensed by the user in the intended way. As a result of the voltage measurement module 150 measuring a low voltage level, a support or maintenance charging instead will be initiated when the voltage level drops to or below the second level. As soon as the first voltage level is reached again the charging is stopped. The voltage drop between the first level and the second level is at a level that will not impair the feedback discharge. The support or maintenance charging will be initiated repeatedly when the voltage level reaches the second level.

Charging Module

The internal structure of the charging module 125 and the capacitor charging module 125 may preferably include a voltage transformation circuit to step up a battery voltage of a handful of volts to a suitable charging voltage of maybe up to a couple of hundred volts.

Stimulating Signal Structure

The stimulator is configured to provide the stimulating signal as a pulse train of one or more pulses. The processor and/or the discharge switch module 160, 161 may be configured to release the discharge in a one pulse fashion only. However, inventors have surprisingly found that a stimulus signal of two to four pulses of 1-10 milliseconds length and 5-20 milliseconds periods of zero voltage in between may generate a sensation suitable for its purpose. The stimulator thus may be configured to provide a discharge voltage preferably in the interval of 2 V to 450 V, and more preferred in the interval of 200 to 450 V. The stimulator may be configured to provide a stimulus signal that does not violate statutory requirements for medical equipment.

Body Impedance Measurements

The stimulator may further be provided with a body impedance measurement module to measure body impedance between the two skin electrodes 135, 137. The body impedance measurement module 155 being coupled to the processor and also to the first and second body electrodes or to one electrode and to ground. Preferred topological arrangements are shown in FIGS. 1a, 1b and 1c.

FIG. 1a shows a block diagram of a stimulator where an impedance measurement module 155 arranged electrically between the charging module 125 and the body first electrode 135. The processor is configured to control the charging module 125 to provide a pulsed voltage that can be used for measuring. The processor is preferably configured to control the discharge switch module 160 connected to ground to allow current to flow in this case.

FIG. 1b shows a block diagram of a stimulator where an impedance measurement module 155 is arranged electrically between the discharge module 161 and a body electrode 137. The device is configured such that charging module provides a low voltage, typically around 5 Volts, to allow the impedance measurement module to measure impedance. The device is configured such that the discharge module connects the charging module and the impedance measurement module to allow current to flow.

FIG. 1c shows a block diagram of a stimulator where an impedance measurement module 155 is arranged electrically between the charging module 125 and the discharge module 161. In this case the stimulator device is configured to let the discharge switch module 161 connect the impedance measurement module 155 to the electrode 137 and current flows from the charging module and the charge holding capacitor 139 through the switch and to the body electrode 137 through the body skin portion and to the electrode 135 and to ground.

The processor is preferably configured to adapt the voltage of the stimulus signal based on measurements of the body impedance from the body impedance measurement module.

For example, a higher impedance measurement may be used by the processor to direct the capacitor charging module 125 to provide a higher voltage to produce a stimulus current equivalent to a case of lower body impedance and lower voltage. The body impedance measurement module may be realised as a separate module or being realised using the voltage measurement module 150 and providing a measurement signal via the capacitor charging module. The capacitor charging module 125 in such case being configured to provide such a measurement signal.

While certain illustrative embodiments of the invention have been described in particularity, it will be understood that various other modifications will be readily apparent to those skilled in the art without departing from the scope and spirit of the invention. Accordingly, it is not intended that the scope of the claims appended hereto be limited to the description set forth herein but rather that the claims be construed as encompassing all equivalents of the present invention which are apparent to those skilled in the art to which the invention pertains.

LEGEND

100 Stimulator
110 Processor

120 Memory
125 Charging module
130 Measurement switch
135 First skin electrode
137 Second skin electrode
138 Transformer device
139, C1 Charge holding capacitor
140 Body skin portion
150 Voltage measurement module
152 Analog to digital converter
155 Impedance measurement module
160 Discharge module
161 Discharge switch module
165 First transistor (Measurement switch)
167 First control resistor (Measurement switch)
168 Second transistor (Discharge switch)
169 Second control resistor (Discharge switch)
199 Diode
C0 Capacitor
R1, R2 etc Resistances

The invention claimed is:

1. A training aid stimulator comprising:
a first skin electrode for making electrical contact to a body of a user;
a second skin electrode for making electrical contact to the body of the user;
a charging module connected to a capacitor equivalent;
a discharge switch module for controlling a feedback discharging of an electric charge;
a processor connected to the charging module for controlling the charging of the capacitor equivalent to a predetermined first voltage level, the processor further being connected to the discharge switch module for controlling the feedback discharging of the electric charge through the first skin electrode and the second skin electrode;
a voltage measurement module for measuring a level of charge of the capacitor equivalent; and
a body impedance measurement module configured to measure a body resistance of the user,
wherein the processor is configured for keeping the training aid stimulator ready to discharge by repeatedly measuring the level of charge of the capacitance equivalent, and by providing a maintenance charging by activating the charging module when a voltage of the capacitor equivalent, is at or below a predetermined second voltage level,
wherein the training aid stimulator being configured to:
disconnect the voltage measurement module when a first voltage level is reached;
wait a predetermined period of time; and
re-connect the voltage measurement module and provide maintenance charging if a measured voltage level is at or below a second voltage level, and
wherein the processor is configured to adapt a voltage of a stimulus signal based on the measured body resistance.

2. The training aid stimulator of claim 1, wherein the training aid stimulator is configured to handle the capacitor equivalent as if the capacitor equivalent is constituted to a major portion of an inherent body capacitance, $C_{BODY}$, of the user.

3. The training aid stimulator of claim 1, wherein the capacitor equivalent is a capacitor.

4. The training aid stimulator of claim 3, wherein the discharge switch module is arranged in an electrical coupling between the capacitor and any skin electrode effectively isolating the body of the user from the capacitor, when not discharging.

5. The training aid stimulator according to claim 1, further comprising a measurement switch for connecting and disconnecting the voltage measurement module, wherein the processor further is configured to repeatedly switch on and switch off the measurement switch.

6. The training aid stimulator according to claim 1, wherein the stimulator is configured to provide a discharge signal comprising one pulse by closing and opening the discharge switch module once.

7. The training aid stimulator according to claim 1, wherein the training aid stimulator is configured to provide a discharge signal comprising two or more pulses by closing and opening the discharge switch module repeatedly.

8. The training aid stimulator according to claim 1, wherein the training aid stimulator being configured to provide a discharge signal comprising two, three or four pulses of 1-10 milliseconds length and 5-20 milliseconds periods of zero voltage in between.

9. The training aid stimulator according to claim 1, wherein the body impedance measurement module is arranged electrically such that the charging module can be used to provide a test voltage for the measurement of the body resistance of the user.

10. A method for keeping a training aid stimulator prepared to deliver a biofeedback electrical stimulus to a body of a user via body electrodes, the method comprising:
applying a charging voltage to a capacitor equivalent;
measuring, using a voltage measurement module, a voltage over the capacitor equivalent, the voltage corresponding to a charging level;
disconnecting the voltage measurement module when a first voltage level is reached;
waiting a predetermined period of time;
re-connecting the voltage measurement module, and providing maintenance charging if a measured voltage level is at or below a second voltage level;
measuring a body resistance of the user using the training aid stimulator; and
adapting a voltage of a stimulus signal based on the measured body resistance.

11. A method for providing a biofeedback electrical stimulus to a body of a user via body electrodes, the method comprising:
applying a charging voltage to a capacitor equivalent;
measuring, using a voltage measurement module, a voltage over the capacitor equivalent, the voltage corresponding to a charging level;
disconnecting the voltage measurement module when a first voltage level is reached;
waiting a predetermined period of time;
re-connecting the voltage measurement module, and providing maintenance charging if a measured voltage level is at or below a second voltage level;
at proper timing, discharging the capacitor equivalent through the body of the user;
measuring a body resistance of the user using the training aid stimulator; and
adapting a voltage of a stimulus signal based on the measured body resistance.

* * * * *